(12) United States Patent
Melton et al.

(10) Patent No.: US 7,337,998 B2
(45) Date of Patent: Mar. 4, 2008

(54) SYSTEM FOR COMMINUTION OF MULTIPLE SAMPLES OF BIOLOGICAL SPECIMENS

(75) Inventors: Scott A. Melton, Erie, IL (US); James E. McCambridge, Polo, IL (US); Steve Arndt, Geneseo, IL (US); Dennis L. Miller, Dixon, IL (US); Terri Stripling, Greenfield Ctr., NY (US); Jeff Karker, Cazenovia, NY (US)

(73) Assignees: Wahl Clipper Corporation, Sterling, IL (US); DrugRisk Solutions, LLC, Schuylerville, NY (US)

( * ) Notice: Subject to any disclaimer, the term of this patent is extended or adjusted under 35 U.S.C. 154(b) by 300 days.

(21) Appl. No.: 11/079,860

(22) Filed: Mar. 14, 2005

(65) Prior Publication Data

US 2006/0202068 A1    Sep. 14, 2006

(51) Int. Cl.
   *B02C 19/00*    (2006.01)
(52) U.S. Cl. .................. 241/100; 241/2; 241/141; 241/169.1; 241/169.2; 241/285.2
(58) Field of Classification Search ............... 241/2, 241/301, 169.2, 169.1, 141, 100, 285.2
See application file for complete search history.

(56) References Cited

U.S. PATENT DOCUMENTS 3,941,317 A * 3/1976 Kanor .................. 241/21
4,828,395 A * 5/1989 Saito et al. ............ 366/143

* cited by examiner

Primary Examiner—Mark Rosenbaum
(74) Attorney, Agent, or Firm—Greer, Burns & Crain, Ltd.

(57) ABSTRACT

An apparatus for comminuting biological specimens includes a receiving component provided with a drive source, at least one sample retainer configured for accommodating at least one biological specimen and constructed and arranged for engagement in the receiving component. The sample retainer includes a first component configured for receiving a specimen prior to comminution and a second component for receiving the specimen after comminution. In addition, the sample retainer is insertable into the receiving component as a single piece.

8 Claims, 9 Drawing Sheets

SYSTEM FOR COMMINUTION OF MULTIPLE SAMPLES OF BIOLOGICAL SPECIMENS

BACKGROUND OF THE INVENTION

The present invention is generally related to methods and apparatus for comminuting biological specimens onsite or in a laboratory, and is more particularly related to devices used for providing biological specimens for subsequent chemical analysis.

For the purposes of this application, the term "comminution" will be understood to mean to mechanically reduce to powder, pulverize, grind, shred, tear or otherwise increase the surface area of biological specimens including, but not limited to hair, feathers, nails, hooves, claws, horns, fur, beaks, scales and other sources of keratin, (or access to the cortex of the specimen), as well as bone, tissue, organs and/or muscle found in humans and animals (hereinafter referred to as biological specimens or samples), whether or not in the presence of a carrier liquid, so that the specimen is readily subject to extraction or detection of drugs and their metabolites, compounds, chemicals or other pharmacologic agents. Testing may also be undertaken to monitor patients' overall health, vitamin deficiencies, effects of exposure to certain chemicals, and other purposes.

Increased drug abuse in North America has been associated with criminal activities, health problems, newborn addiction, lost worker productivity and staggeringly high medical costs. Currently of greatest concern are opiates (heroin, morphine, codeine), cocaine, marijuana, MDMA (Ecstasy), phencyclidine, amphetamine and methamphetamine.

Possible pesticide residues in the breast tissues of women and the concern over the presence of synthetic agents and compounds in plant and animal foodstuffs has raised concerns about possible environmental exposure including air- and water-borne agents, as well as, exposure of domestic animals to agricultural chemical agents such as pesticides and herbicides, growth hormones and/or antibiotics. Verifying a natural "organic" status prior to slaughter has, thus, recently become of significant interest.

In testing for human drugs of abuse, several test systems are presently marketed for detecting drug analytes in urine e.g., ONTRAK™ and ONLINE™ (Roche Diagnostic Systems, Inc.), the ADx™ automated fluorescence polarization immunoassay system (Abbott Laboratories, Inc.) and EZ-SCREEN™ (Environmental Diagnostics). Unfortunately, there are significant problems associated with urine testing for drugs of abuse, e.g., (i) possible false positive results for opiates recorded in subjects who are on certain medications and who have recently ingested poppy seeds; (ii) rapid elimination rates and short half-life of many drug metabolite compounds; and particularly (iii) false negatives associated with purposeful adulteration, dilution, urine substitution and other creative ways donors discover to beat a drug test.

Unlike liquid urine samples, solid samples such as hair require special sample preparation prior to conducting assays. Conceptually, hair provides a better toxicological specimen than urine, serum, sweat or saliva because its relatively slow growth increases the period of time during which drug usage is detectable. Human head hair grows approximately $\frac{1}{64}$ (0.016) inch per day, thus creating a calendar of drug use. It takes about seven (7) days after ingestion of drugs for the drugs to be extractable from hair outside the scalp. Approximately 1.5 inches of human head hair can show drug usage over a ninety (90) day period. The hair can also be sectioned into periods of thirty (30) day use.

In present day practice, extraction of drugs from hair often involves cutting the hair into small pieces using razor blades or scissors and inserting the cut hair into a test tube where it is then exposed to acid and/or base hydrolysis, prolonged enzymatic digestion, heat, organic solvent extraction and/or sonication. The cutting procedure is labor intensive, time consuming and is subject to the particular cutting techniques of individual technicians. Also, when multiple specimens need to be analyzed, technicians are subject to repetitive stress injuries. These methods require technical experience and are presently most easily conducted in a test laboratory. However, even then the sample process can take two to three hours to complete, and the results are not available for as long as seven days, the samples frequently suffer from poor reproducibility, there are long delays before results can be released and, even then, variability occurs in the ability to isolate different drugs and their metabolites. Hydrolysis conditions can also result in conversion of drug metabolites such as 6-monoacetylmorphine, whose presence provides judicial proof of drug abuse, into parent compounds, i.e., morphine. Fortunately, it has been found that certain drugs and their metabolites can persist in hair for extended periods of time.

Another method for preparing a sample of hair for chemical analysis is for a technician to freeze dry the sample using liquid Nitrogen, then grind the frozen hair in a mortar and pestle for 5 to 10 minutes until it is powdery in appearance. This comminution or maceration operation is useful for increasing the surface area of the hair and, thus reducing the reaction time of the analytical chemicals on the sample and increasing extractability of the agents of interest. Using this method the amount of prepared specimen obtained for analysis may vary by sample as well as by individual technician, and the liquid Nitrogen limits usage to a laboratory setting. An alternative procedure for comminution involves a ball mill, but that device inherently has contamination issues with the balls from sample to sample, and is thus only useful in a laboratory process and this method of comminution is relatively slow.

There is a need for a rapid mechanical comminution method and apparatus for biological specimens which is easily adapted to both portable on-site comminution and laboratory comminution to prepare samples for detection of the agents of interest. There is also a need for a comminution method and apparatus for such specimens which is repeatable on an objective basis, maximizes sample integrity by eliminating cross contamination between specimens, increases the surface area of the hair and exposes the cortex of the hair for increased and rapid extractability of the agents of interest.

BRIEF SUMMARY OF THE INVENTION

The above-identified needs are met or exceeded by the present apparatus for the comminution of biological specimens, which provides a receiving unit and a preferably disposable sample retainer that can be inserted into the receiving unit in one piece. As such, the specimen to be comminuted, and the comminuted product, are installed and removed from the receiving unit as one piece to increase processing efficiency and to reduce the potential for cross-contamination of specimens. In the preferred embodiment, the sample retainer includes comminution elements which reduce the specimens to a granular or powder-like state for more efficient and rapid detection for the agents of interest.

The preferred receiving unit is provided with a drive system for powering the comminution of at least one and preferably multiple specimens. Further, the receiving unit is preferably configured for enhancing the collection of ground specimen from the sample retainer.

More specifically, an apparatus for comminuting biological specimens includes a receiving component provided with a drive source, at least one sample retainer configured for accommodating at least one biological specimen and constructed and arranged for engagement in the receiving component. The sample retainer includes a first component configured for receiving a specimen prior to comminution and a second component for receiving the specimen after comminution. In addition, the sample retainer is insertable into the receiving component as a single piece.

In another embodiment, a machine for comminuting multiple biological specimens is provided, each specimen being provided in a sample retainer including a first component configured for receiving a specimen prior to comminution, a second component for receiving the specimen after comminution, and a ram element. The machine includes a drive source, a plurality of drive collars configured for being driven by the drive source, each drive collar configured for receiving a corresponding sample retainer, and a plurality of ram keys each corresponding to one of the drive collars and configured for exerting a biasing force on a corresponding ram element for causing comminution of a sample in the sample retainer.

In yet another embodiment, a sample retainer for use with a machine for comminuting biological specimens is provided, the machine including a drive source, a plurality of drive collars and a like plurality of ram keys. The sample retainer includes a cup, a funnel joinable to the cup, at least one comminution surface associated with at least one of the cup and the funnel, and upon joining, the cup and the funnel being insertable into the machine as a unit.

DETAILED DESCRIPTION OF THE INVENTION

Figure 1:
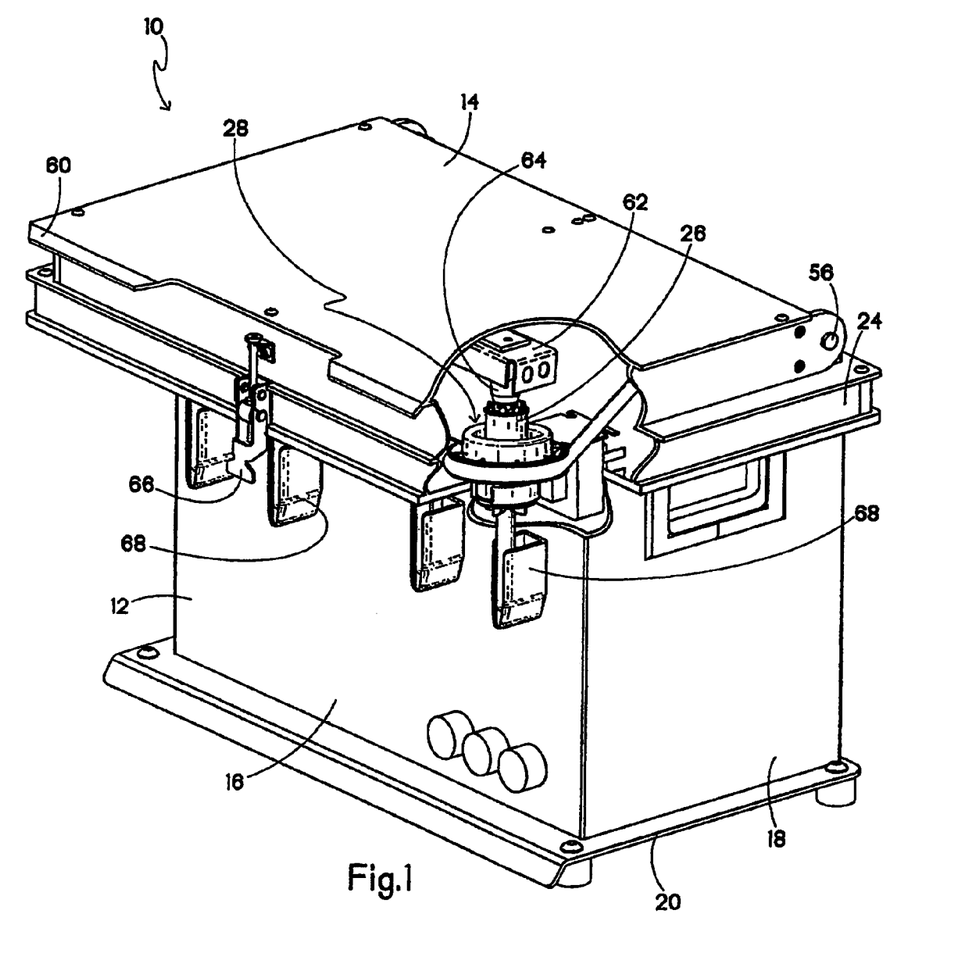
FIG. 1 is a top perspective view of the present comminution apparatus with portions omitted for clarity.

Referring now to FIGS. 1, 2A, 2B and 4B, an apparatus or device for comminuting biological specimens or samples is generally designated 10 and is intended for comminuting specimens or samples such as hair, nails, fur, feathers, hooves or other materials having keratin, as well as other biological products such as muscle, organ and/or bone or which are known or believed to contain compounds accessible through chemical analysis and other detection systems. While the present apparatus 10 is depicted in a configuration for processing multiple specimens at a time, it is contemplated that, depending on the application, a single specimen may be comminuted in the apparatus. In the preferred embodiment, the apparatus 10 is configured for placement upon a table or other work surface, and the use of terms such as "top", "bottom", "upper" and "lower" refer to the apparatus 10 oriented as depicted in FIG. 1, however other orientations are contemplated depending on the application.

Figure 2A:
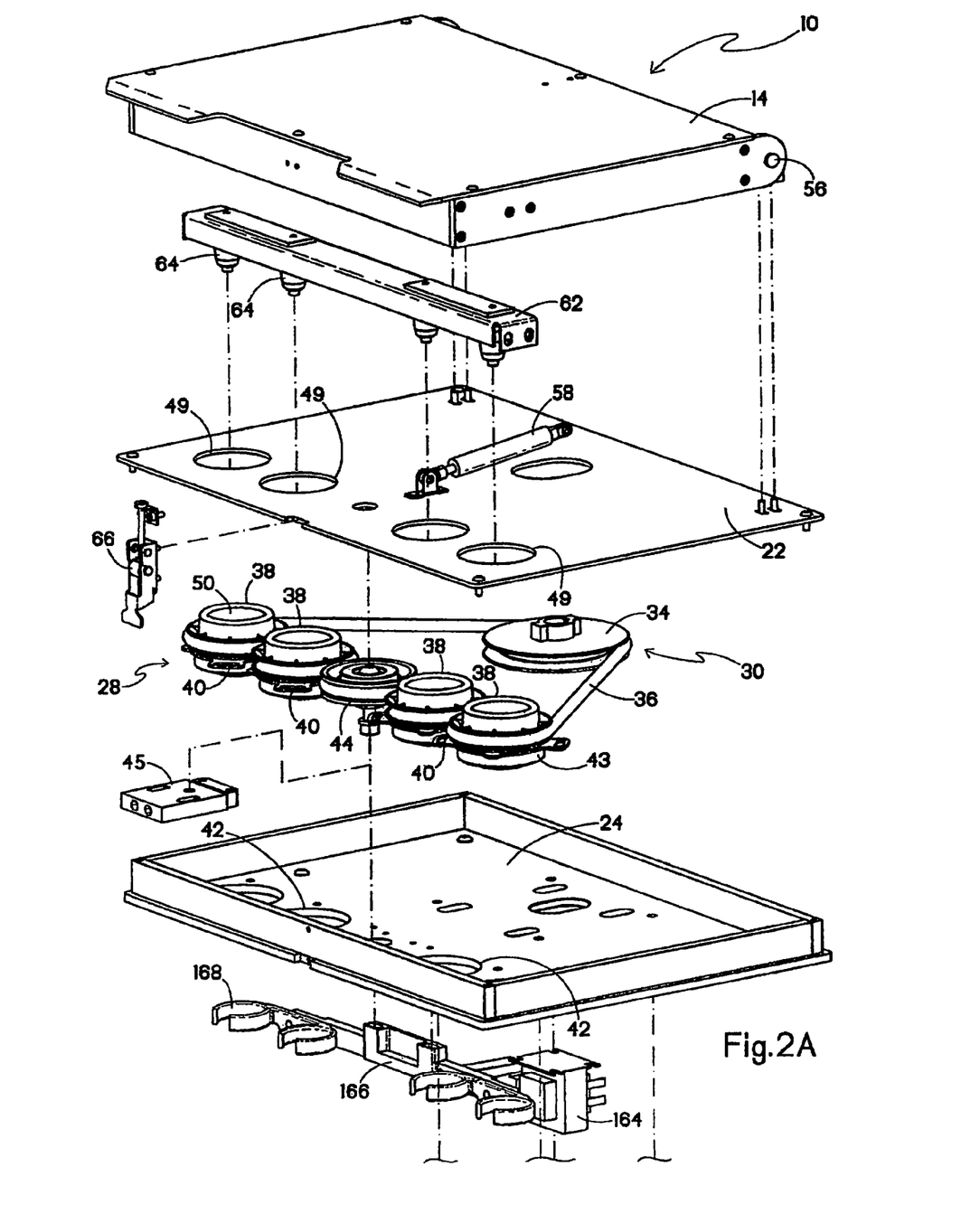
FIG. 2A is an upper half of an exploded perspective view of the apparatus of FIG. 1.
Figure 2B:
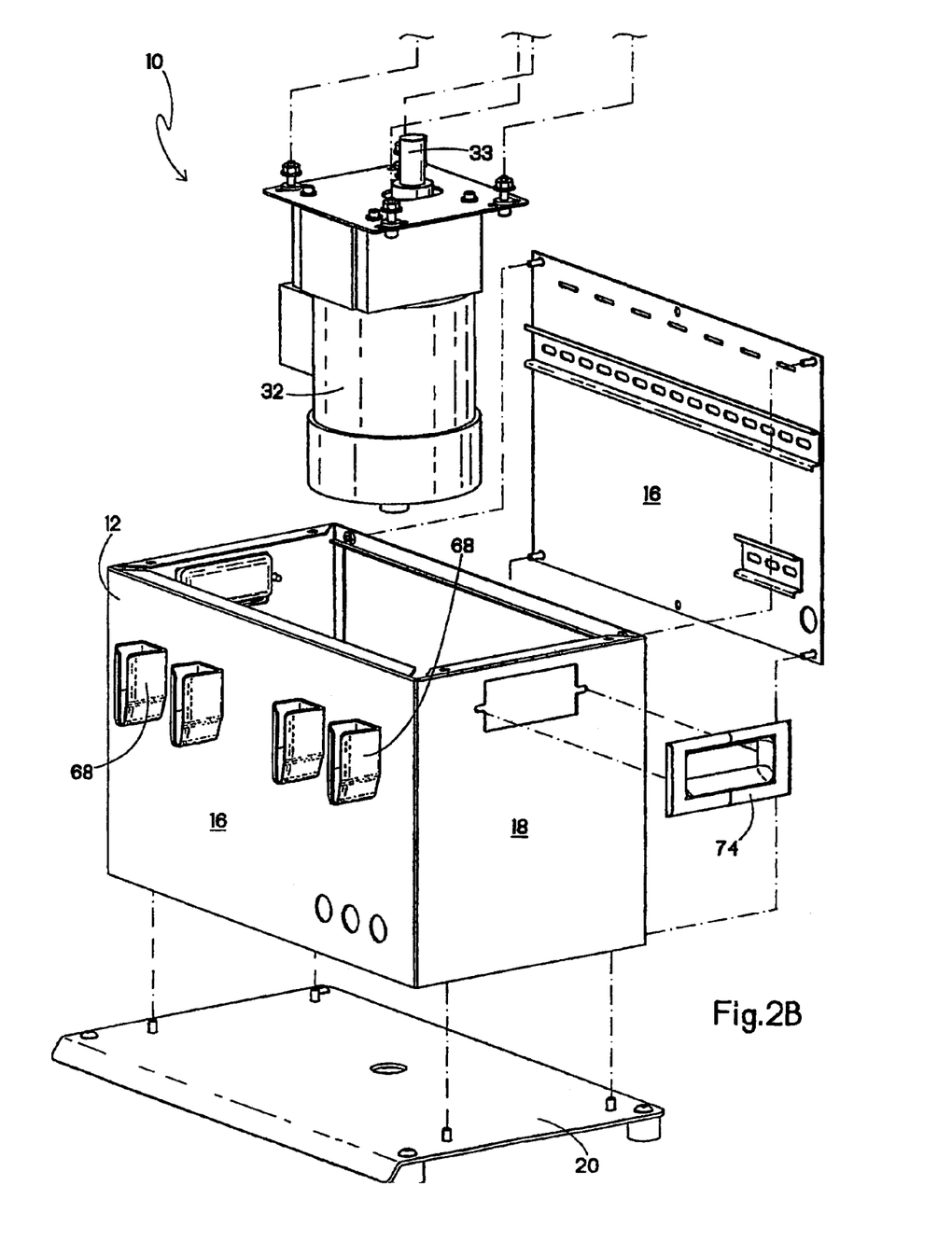
FIG. 2B is a lower half of an exploded perspective view of the apparatus of FIG. 1.

More specifically, the apparatus 10 preferably includes a housing or cabinet 12 having a lid 14, two sidewalls 16, two endwalls 18 and a bottom 20. While the cabinet 12 is shown as box-like, other shapes are contemplated depending on the application. As is known in the art, one or more of the side or endwalls 16, 18 may be readily removable for access to the interior for adjustments, repairs and the like. Also included on the cabinet 12 are a base plate 22 and a drive support tray 24.

Preferably configured for receiving and processing sample retainers, generally designated 26, provided in a unitary or one-piece format, the apparatus 10 is also designed for processing or comminuting multiple sample retainers simultaneously. A sample retainer-receiving component, generally designated 28 is supported within the cabinet 12 upon the drive support tray 24 below the base plate 22, and is operationally connected to a drive source 30, made up in part of a motor 32 (FIG. 2B) preferably an electric motor having a drive shaft 33 and located within the cabinet 12 below the support tray 24. However, the type of motor 32 and its location may vary to suit the application. In the preferred embodiment, the drive source 30 includes a drive pulley 34 operationally connected to the drive shaft 33 as is known in the art and, upon assembly located above the support tray 24.

Figure 12:
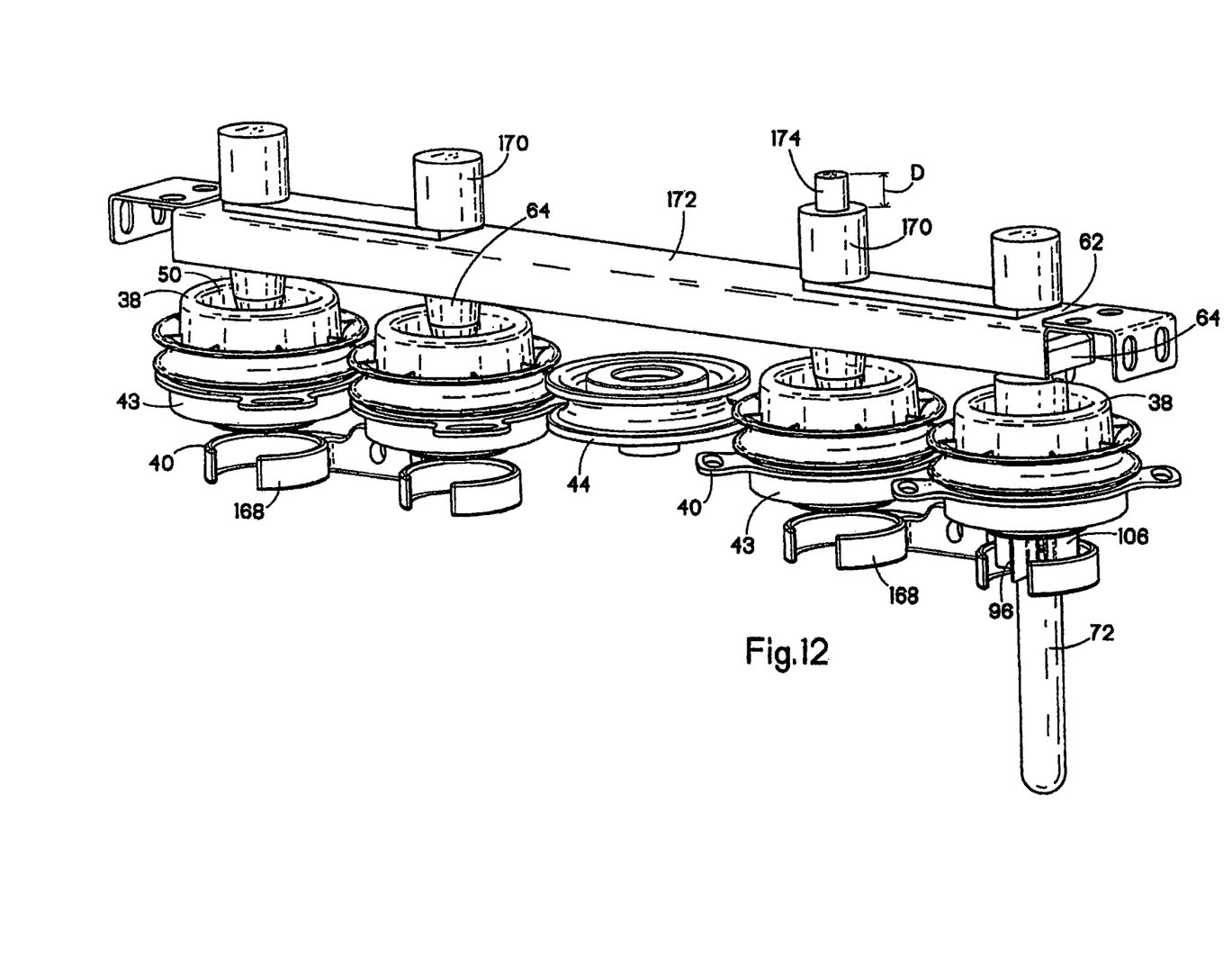
FIG. 12 is a fragmentary top perspective view of the assembled ram key, sample retainer and drive assembly of the present apparatus.

Referring now to FIGS. 2A and 12, a serpentine drive belt 36 is engaged on the drive pulley 34 and around a plurality of drive collars 38. While the present pulley and belt drive source 30 is preferred, it is contemplated that a gear drive, chain and sprocket arrangement, individual motors for each collar, or even a pneumatic powered turbine system would be suitable for driving the drive collars 38. In the preferred embodiment there are four drive collars 38, however the number and arrangement of the drive collars may vary to suit the application. The drive collars 38 are preferably linearly aligned on the support tray 24 and rotatably engage collar bearing saucers or retainer rings 40 mounted to corresponding collar bores 42 in the support tray. Each retainer ring 40 encloses a ball bearing 43 for facilitating rotation of the collar 38 relative to the retainer ring and for the mounting of the bearing to the tray 24. To facilitate location of the collar 38 in the ball bearing 43, each collar 38 is preferably located with a key rib 41 (FIG. 4B) which keys into a corresponding receptacle on the ball bearing.

Also included in the drive source 30 is an idler pulley 44 rotatably secured to the support tray 24 and slidably adjustable as is known in the art to adjust the tension of the drive belt 36. The drive belt 36 is threaded around the idler pulley 44, which is preferably located midway between the four drive collars 38, however its location may vary to suit the application provided the function of belt tensioning is achieved. A pulley tensioner 45 is provided for allowing user adjustment to the tension on the drive belt 36.

Figure 6:
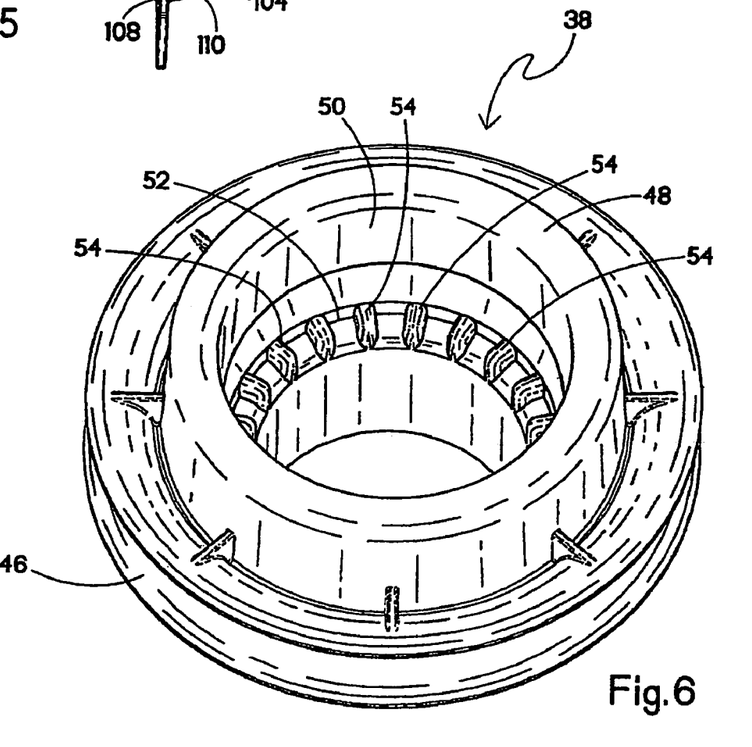
FIG. 6 is a top perspective view of the receiving device depicted in FIGS. 3B and 4B.

Referring now to FIG. 6, each drive collar 38 is provided with a drive belt groove 46 around an outer periphery, constructed and arranged for receiving the drive belt 36, and an axially projecting support ring 48 which projects through a corresponding opening 49 in the base plate 22 and also defines a central throughbore 50. The throughbore 50 is coaxial with the collar bores 42 of FIG. 2A. A counterbore 52 in the throughbore 50 defines a shoulder upon which are located a plurality of spaced, radially oriented teeth 54. Once assembled, the drive source 30 is protected by the base plate 22, which is secured to the support tray 24 by conventional removable fasteners. Upon assembly of the drive source 30, and activation of the motor 32, rotation of the drive pulley 34 will cause simultaneous rotation of the drive collars 38 through action of the drive belt 36.

Returning now to FIGS. 1, 2A and 2B, the lid 14 is supported upon the base plate 22 by a hinge 56 and a conventional dampening cylinder 58 mounted to the underside of the lid and to the base plate in a conventional manner. The cylinder 58 prevents the lid 14 from falling upon the technician's hands or arms during installation and retrieval of the sample retainers 26. Also provided on the lid 14 is at least one handle 60 constructed and arranged to facilitate closure by a technician.

A ram key rack 62 is mounted to the underside of the lid 14 and defines a downward-opening, generally "U"-shaped channel. Into the channel are mounted a plurality of ram keys 64 (best seen in FIG. 11), the number of which corresponds to the number of drive collars 38. Preferably, the ram keys 64 are each disposed in the rack 62 to be coaxial with the corresponding central throughbore 50. The operation of the ram keys 64 will be described in greater detail below.

Also provided on the cabinet 12 is a latch 66 for securing the lid 14 to the base plate 22 and the drive support tray 24. Below the drive support tray 24, a plurality of sample collector receiving pockets 68 are secured to the front sidewall 16 of the cabinet 12, preferably to the underside of the tray, and each pocket is constructed and arranged for receiving and supporting a corresponding sample collector, generally designated 72, which is part of each sample retainer 26. Lifting handles 74 (FIG. 2B) are provided as desired on the cabinet 12 to facilitate portability of the apparatus 10.

Referring now to FIGS. 3A, 3B, 4A and 4B, the sample retainer 26 will be described in greater detail. The sample retainer 26 includes a first component or cup 80 configured for receiving a specimen prior to comminution. In the preferred embodiment, the cup 80 is a generally cylindrical sleeve defining an axially extending throughbore 82. A lower end 84 is configured as a skirt extending radially from the wall of the cup 80.

The throughbore 82 is closed off by a comminution material disk 86 forming a first comminution surface. In the preferred embodiment, the disk 86 is generally planar and made of perforated metal made from, or using techniques known in the electric shaver art for producing electric shaver foil having apertures in the approximate range of 0.025 inch, however the size and shape of the openings in the disk may vary to suit the application, provided they are large enough to pass comminuted hair fibers therethrough. Human hair fibers typically have a diameter in the range of 0.002-0.004 inch. While a shaver foil or similar perforated disk is the preferred material and construction for the comminution surface 86, it is contemplated that other materials would be suitable provided they produce comminuted hair, feathers, nails, hooves, horns, fur, beaks, and other sources of keratin or other specimens found in humans and animals suitable for chemical analysis and other detection systems.

Figure 9:
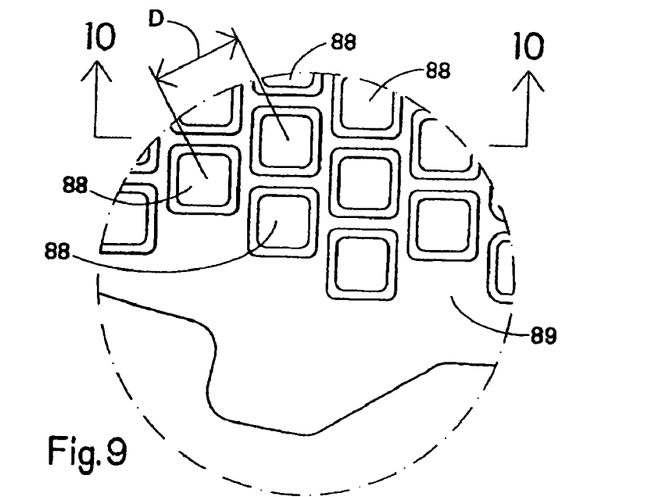
FIG. 9 is an enlarged fragmentary plan view of a second type of comminution surface suitable for use with the present sample retainer.
Figure 10:
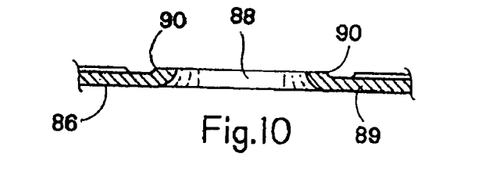
FIG. 10 is a section taken along the line 10-10 of FIG. 9 and in the direction generally indicated.

Referring now to FIGS. 9 and 10, an exemplary pattern of comminution bosses 88 is depicted. The bosses 88 are produced by electroforming, photoetching, stamping or similar techniques known in the shaver foil art to project axially from a plane 89 defined by the surface 86, and are formed in a generally square or polygonal shape, however it is contemplated that the shape may vary to suit the application. Through the manufacturing process, the bosses 88 have sharp outer edges 90 which perform the comminution. While other spacing is contemplated, depending on the situation and the subject matter to be comminuted, it has been found that a spacing of approximately 0.028 inch between center points of adjacent bosses 88 (distance "D" in FIG. 9) has provided positive results. Also, the bosses 88 preferably have a height equal to or less than the diameter of human hair fibers. However, the height of the bosses 88 may vary to suit the application, and all bosses may not necessarily have the same height.

Referring again to FIGS. 3A, 3B, 4A, 4B and 5, since the disk 86 is made of relatively thin material, it is preferred that it be supported in the sample retainer 26. This support is provided by a support grid 92 made up of first and second pluralities of spaced bars 93 oriented preferably normally to each other or radially or in other orientations so that a supportive yet porous surface is obtained. The grid 92 is secured within an upper counterbore 94 of a second component of the sample retainer 26, generally designated a funnel 96. The skirt 84 is secured to an exterior of a lip 98 of the funnel 96, located at an upper end 100 of the funnel. Preferably, the attachment of the grid is accomplished by ultrasonic welding the skirt 84 to the lip 98, which captures the disk 86 and the grid 92 in place. However, chemical adhesives or other suitable fastening technologies are contemplated. It is also contemplated that the comminution surface 86 may be integrally formed with the grid 92 and even be made of the same material.

Upon fastening the cup 80 to the funnel 96, the sample retainer 26 is formed into a single piece, which is the preferred form in which it is inserted into the receiving component 28. Additional preferred components of the sample retainer 26 include the sample collector 72, which in the preferred embodiment is a test tube. Among others, suitable test tube sizes include 12×75 mm, 10×40 mm, 13×45 mm, 13×50 mm and 13×60 mm. Alternatively, the known "Hitachi" cups are contemplated sample collectors 72, as well as other laboratory standard test tubes and other holding vessels known to those skilled in the art. However, it is contemplated that other types of containers would be suitable in this application as sample collectors 72.

The funnel 96 is configured for receiving the biological sample after comminution, and as such is tapered toward a lower end 102. To frictionally engage the sample collector 72, the lower end 102 is formed with a generally cylindrical nozzle 104 which tightly engages an inner diameter of the collector 72. Thus, the funnel 96 is contemplated as being designed to correspond with a suitable type of collector. At least three and preferably four fin-like legs 106 are used for enabling the funnel to be self supporting on a substrate such as a laboratory table. At least two of the legs 106 are provided on an inner edge 108 with an arcuate tab formation 110 which complements the nozzle 104 by engaging an outer periphery of the collector 72. The collector 72 is thus sandwiched at its upper end between the nozzle 104 and the tab formations 110 for a snug, friction fit. In the preferred embodiment, the collector 72 is supported on the sample retainer 26 only by its engagement with the funnel 96 as described above.

Figures 3A, 4A:
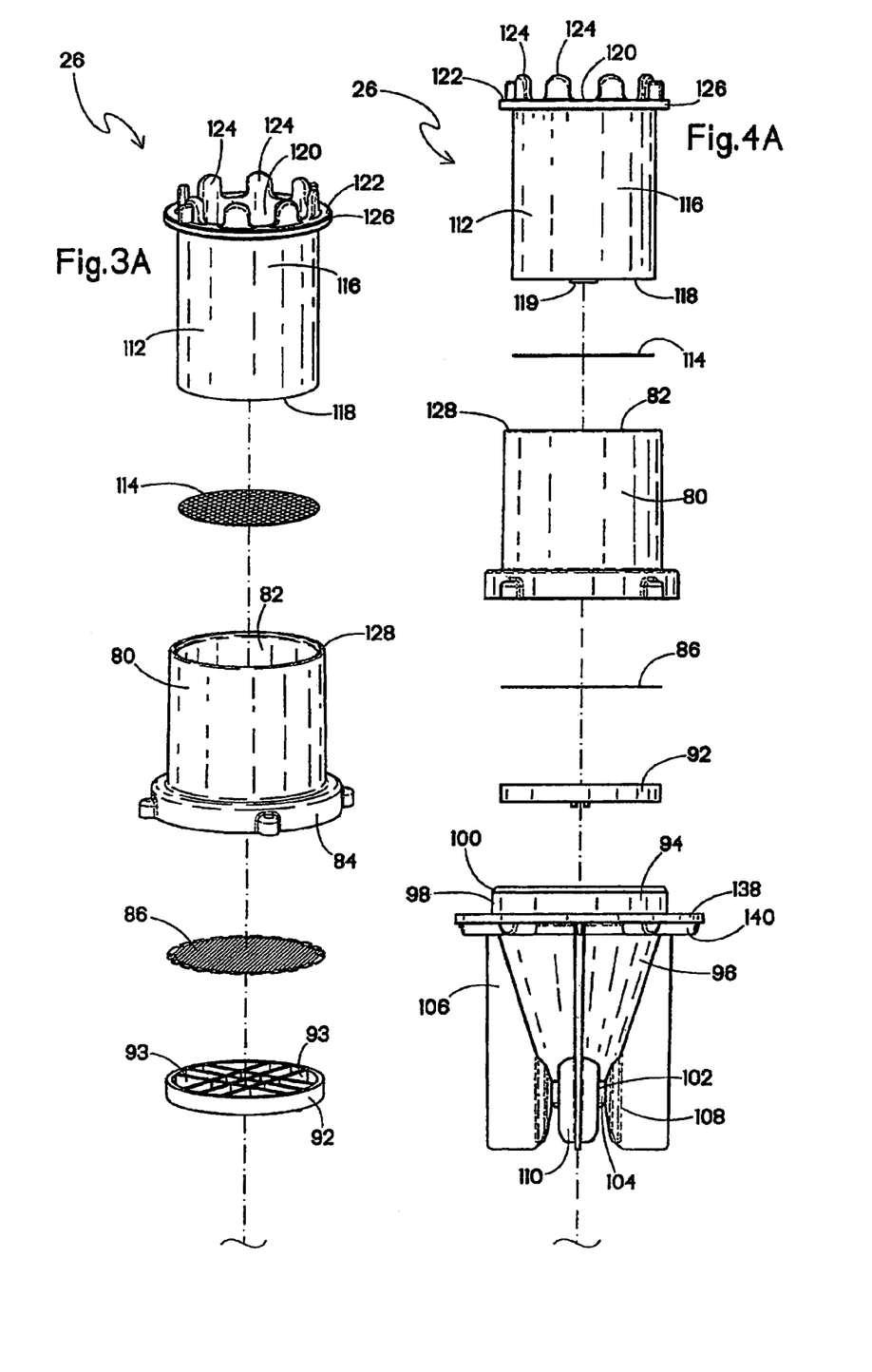
FIG. 3A is an upper half of an exploded perspective view of a sample retainer, ram and sample collector suitable for use with the present apparatus.
FIG. 4A is an upper half of an exploded elevation of the sample retainer and ram depicted in FIGS. 3A and 3B.
Figures 3B, 4B:
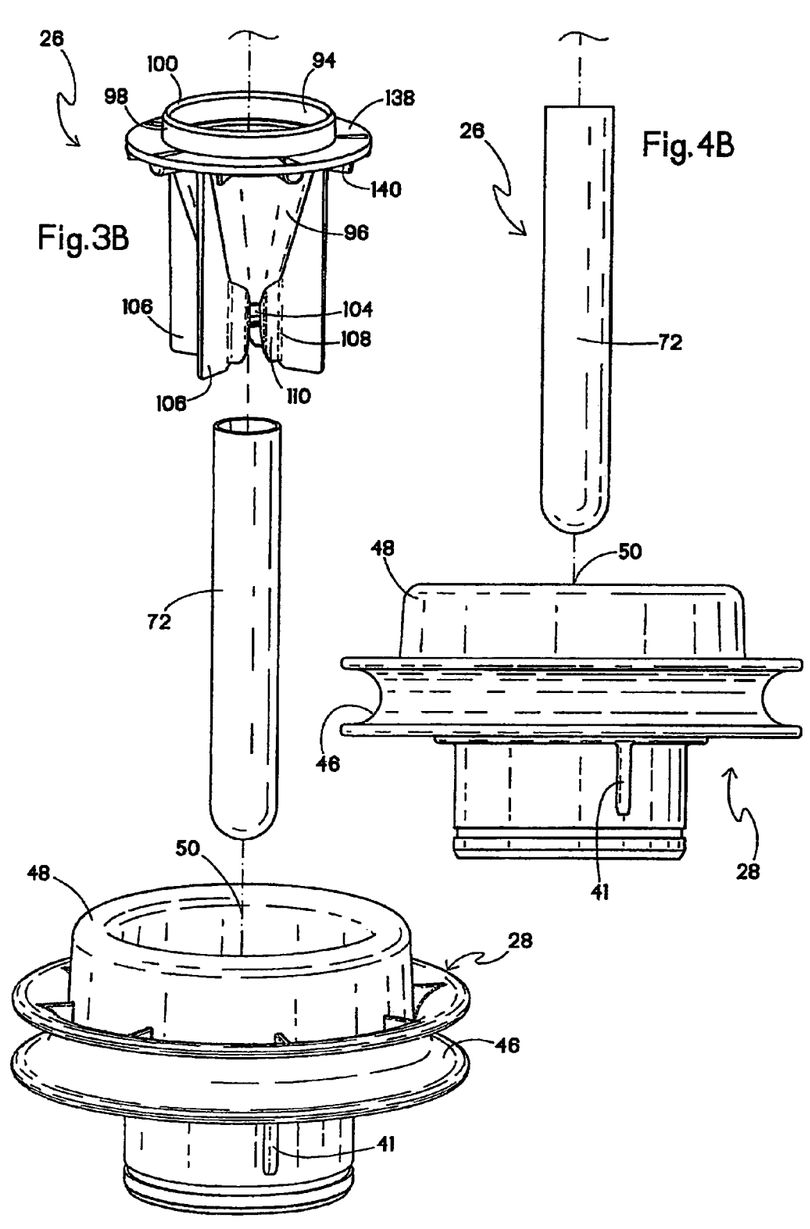
FIG. 3B is a lower half of the exploded perspective view of FIG. 3A, also depicting a portion of the receiving device.
FIG. 4B is the lower half of an exploded elevation of the sample collector and receiving device of FIG. 3B.

Referring now to FIGS. 3A and 4A, in the preferred embodiment, a ram element or ram 112 is part of the sample retainer. The ram 112 is configured to provide a second comminution surface 114 constructed and arranged to move relative to the comminution surface 86 on the cup 80 for comminuting specimens placed therebetween. While other arrangements are contemplated, the first comminution surface 86 moves relative to the second comminution surface 114, and preferably, that movement takes the form of rotation. The cup 80, the funnel 96, the sample collector 72 and the ram 112 are preferably assembled and placed as a unit or a single piece into the drive collar 38 and, with the exception of the ram, rotated therewith.

While admittedly the ram 112 and the sample collector 72 are not permanently fixed to the cup 80 and the funnel 96, for the purposes of this application, they are referred to as being installed into the apparatus 10 as one piece, since they are installed as a unit to be engaged in the drive collar 38. This preferred unitary assembly and handling has been found to reduce cross contamination between samples. As will be described below in greater detail, the ram 112 is held stationary relative to this rotary movement while the sample retainer 26 is engaged in the apparatus 10.

More specifically, the ram 112 has a generally cylindrical body 116 dimensioned to slidably telescope into the axial throughbore 82 of the cup 80 and rotate relative to the throughbore while telescopingly engaged. The second comminution surface 114 is secured to a closed end 118, as by chemical adhesive, sonic welding or similar fastening technology. Alternatively, it is contemplated that the surface 114 may be applied to the closed end 118 by electroplating or electrodeposition, or may be integrally formed on the closed end. An optional depending formation or boss 119 is formed to depend from the closed end 118 to create a slight axial bulge or protrusion in the comminution surface 114. The formation 119 is generally elliptical when viewed in plan and is configured for causing the bulge in the surface 114 to engage the comminution surface 86 at the highest pressure point during operation for preventing accumulation of uncomminuted hair, especially the creation of hair balls in the middle of the comminution surface. The relatively small height of approximately 0.012 inch of the formation 119 does not interfere with the other action of the surfaces 114, 86 relative to each other. It is contemplated that the height and/or shape of the formation 119 may vary to suit the application.

At an opposite, open end 120, a peripheral edge 122 is provided with a plurality of ram teeth 124 projecting along an axis generally parallel to an axis of rotation of the sample retainer 26. The peripheral edge 122 also preferably includes a radially projecting lip 126. In some applications, engagement of the lip 126 upon a corresponding upper end 128 of the cup 80 regulates the relative position of the comminution surfaces 86, 114. It is preferred that some spacing be defined between the surfaces 86, 114 for facilitating comminution of the hair sample. Since the diameter of a typical strand of hair is in the range of 0.002-0.004 inch, favorable comminution results have been obtained when the spacing between the surfaces 86, 114 is in a similar range.

Figure 7:
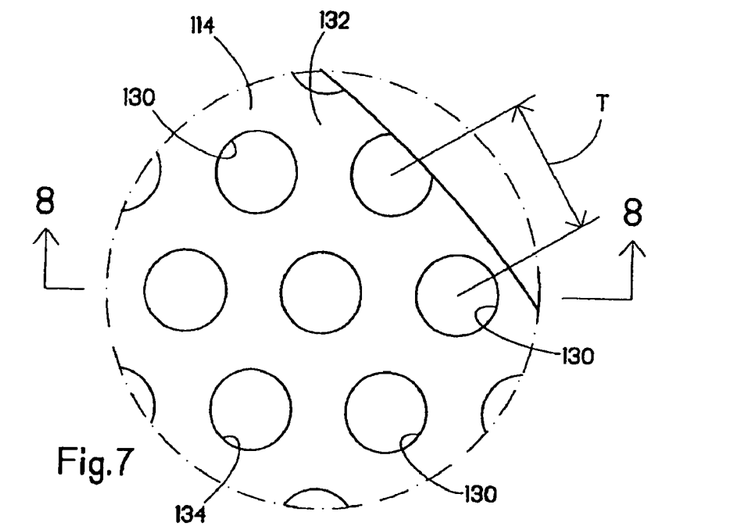
FIG. 7 is an enlarged fragmentary plan view of a type of comminution surface suitable for use with the present sample retainer.
Figure 8:
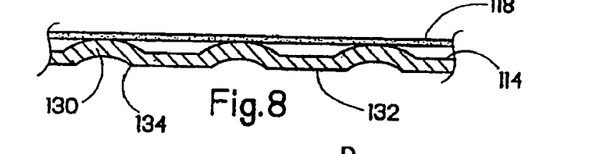
FIG. 8 is a section taken along the line 8-8 of FIG. 7 and in the direction generally indicated.

Referring now to FIGS. 7 and 8, the preferred comminution surface 114 is viewed in greater detail. While other configurations are contemplated depending on the type of biological material to be comminuted, when hair is the desired biological material, the comminution surface is preferably provided with a plurality of spaced, generally circular bosses 130 which are formed by die forming and lapping, or alternatively by electroforming or photoetching onto a generally planar surface 132. Relatively sharp peripheral edges 134 formed in the stamping process perform comminution when moved relative to the surface 86. While other spacings are contemplated, it is preferred that the center-to-center distance "T" between adjacent bosses 130 is approximately 0.064 inch. It is contemplated that the boss height may vary to suit the application or the sample type and size, and that boss height may vary within or upon the same surface 86, 114.

While shaver foil is the preferred material for the surfaces 86, 114, and while the comminution apparatus is presently disclosed in the form of the opposed comminution surfaces, other comminution surfaces or apparatus capable of comminuting hair, feathers, nails, hooves, horns, fur, beaks, and other sources of keratin or other types of specimens found in humans and animals are contemplated. For example, it is contemplated that the surfaces 86, 114 may be made of other materials, including metals such as stainless steel, nickel, aluminum alloys of the above and similar metals, plastics, abrasives such as sandpaper, silica carbide or other suitable abrasive or grinding materials. It is further contemplated that the foil surfaces 86, 114 may be exchanged on the respective cup 80 and the ram 112 and also that the ram may rotate relative to the cup.

Figure 5:
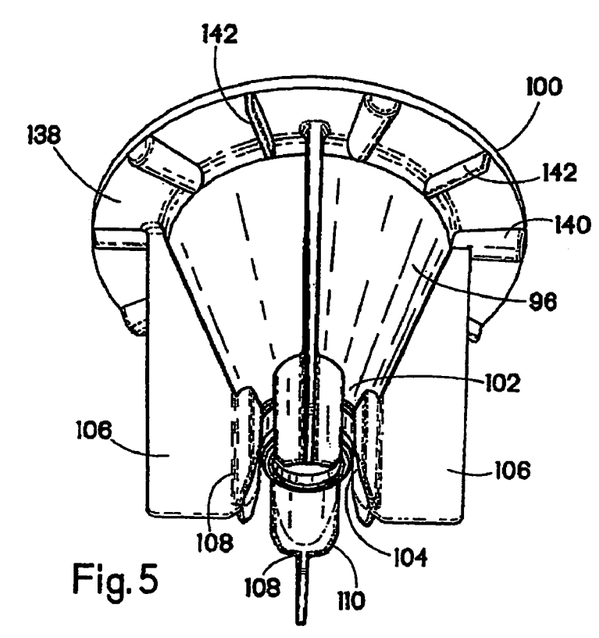
FIG. 5 is a bottom perspective view of the present funnel portion of the sample retainer.

Referring now to FIGS. 5 and 6, the sample retainer 26 is rotated relative to the ram 112 by engagement of the funnel 96 in a corresponding one of the drive collars 38. Opposite the nozzle 104, the funnel 96 is provided at the upper or opposite end 100 with a radially projecting flange 138 having a plurality of spaced, depending, radial extending lugs 140. While the size and spacing of the lugs may vary to suit the application, in the preferred embodiment, each standard or relatively larger size lug 140 alternates with a relatively smaller lug 142. The spacing and configuration of the lugs, 140, 142 is designed to drivingly mesh with the complementary spaced, radially extending teeth 54 of the drive collar (FIG. 6). Upon insertion of the sample retainer 26 into the apparatus 10, the support ring 48 facilitates the location of the funnel 96 into the central throughbore 50 so that the lugs 140, 142 will drivingly engage the teeth 54. Also, the radially projecting flange 138 is matingly received in the throughbore 50 and is circumscribed by the support ring 48.

Figure 11:
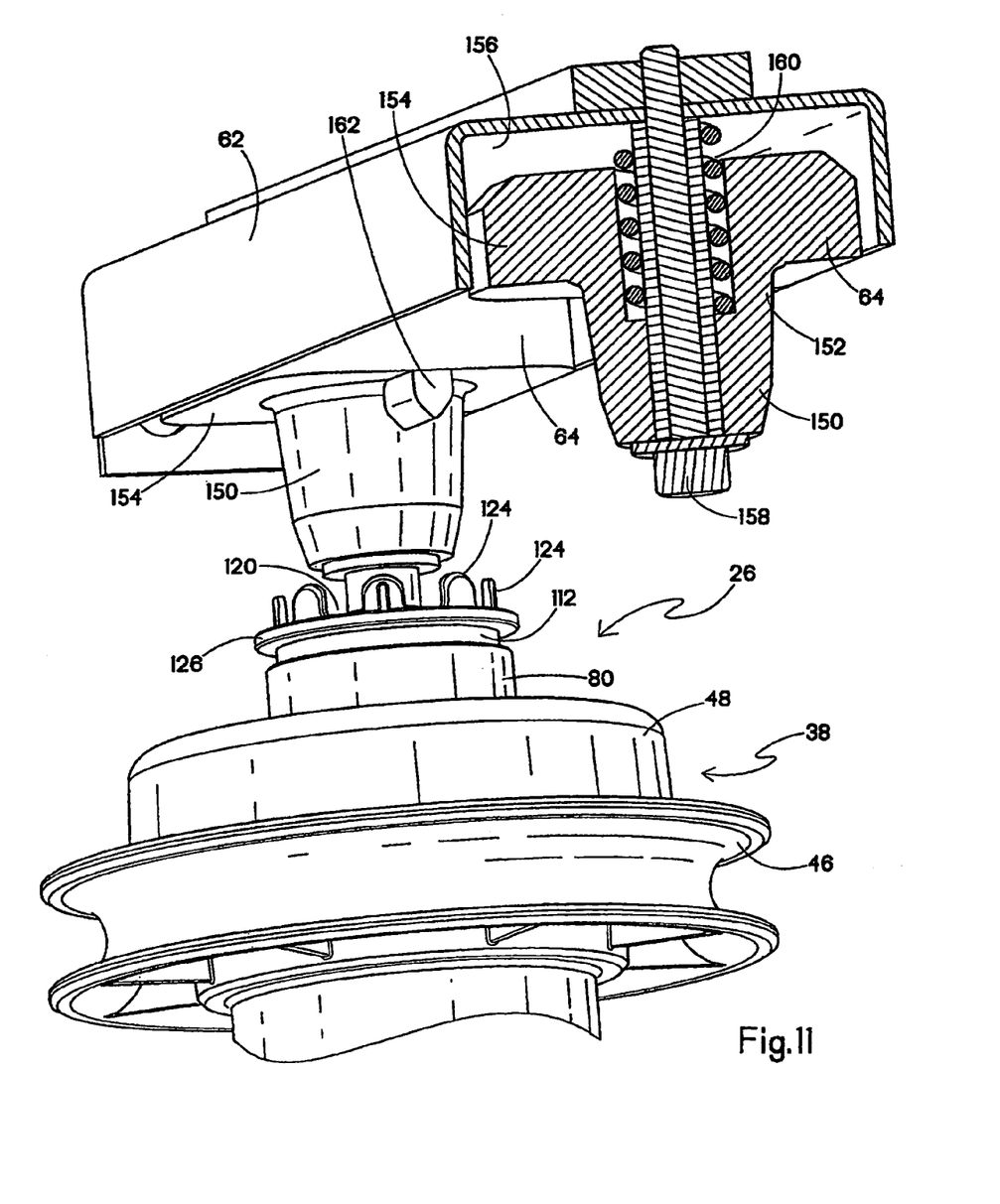
FIG. 11 is a fragmentary bottom perspective view of the apparatus of FIG. 1 showing detail of the ram keys and engagement with the ram.

Referring now to FIGS. 11 and 12, the ram key rack 62 and a pair of the ram keys 64 are shown in greater detail. Each ram key 64 has a generally conical shape, with a tapered end 150 configured for location in the open upper end 120 of the ram 112. A radially flared upper end 152 is joined to a base 154 which abuts an underside 156 of the ram key rack 62. The base 154 is polygonal and preferably is square or rectangular and is of sufficient size so that it is constrained against rotation by the ram key rack 62. A threaded fastener 158 secures the ram key 64 to the rack 62, and a biasing element 160 such as a coiled spring or the like biases the key 64 towards the corresponding drive collar 38. At least one and preferably two diametrically opposed key formations 162 are constructed and arranged to locate between the spaced ram teeth 124.

Once the sample retainer 26 is loaded with a specimen between the two comminution surfaces 86, 114 and is placed in the open drive collar 38, the lid 14 is closed and the biased ram key 64 engages the corresponding ram 112. The ram 112 is thus prevented from rotating relative to the cup 80, the funnel 96 and the sample collector 72 once those components are rotated as the drive collar 38 is rotated by the motor 32. Another function of the biasing element 160 is to urge the ram 112, and the corresponding second comminution surface 114 against the comminution surface 86 and the sample retained therebetween to achieve the desired comminution.

Referring now to FIGS. 2A and 12, it has been found that collection of comminuted biological sample material is enhanced in some applications by vibrating the sample retainer 26 in conjunction with the comminution operation. The vibrations may be induced during or after the comminution action, here preferably obtained through relative rotation of the cup 80 and the ram 112. In the preferred embodiment, the vibration is generated by a solenoid 164 disposed in operational relationship to a linkage bar or arm 166 having a plurality of attached open rings 168. The arm 166 is secured to an underside of the tray 24. As seen in FIG. 12, the rings 168 are each dimensioned to loosely circumscribe a corresponding one of the funnels 96. Vibrations in the form of repetitive "taps" generated by the solenoid 164 are transmitted through the arm 166, the rings 168 and ultimately to the funnels 96. Comminuted specimen particles are thus encouraged to move down through the nozzle 104 of the funnel 96 and into the sample collector 72. The above apparatus is a preferred system for applying vibrations to the sample retainer 26, however it is contemplated that other vibration generators may be employed, such as eccentric tappers, electromagnetic motors, sonic vibrators or similar mechanisms or devices which generate vibrations or shock waves to facilitate the movement of specimens down the funnel 96.

It has been found that the motor 32 is controllable to obtain various types or degrees of comminution. For example, the motor 32, and the corresponding drive collars 38 may be rotated for a specified period of time, and then the sample retainers removed. Alternately, the drive collars 38 may be rotated first in a first direction for a specified period of time, then the direction of rotation can be reversed for another period of time, which can be the same or different from the period of rotation in the first direction. In one embodiment, the direction of rotation and timing is approximately 0.5 second in a first direction, then 0.5 second in a reverse direction. Timing ranges of between about 0.5 to 10 seconds are contemplated. Rotational direction and timing of comminution are contemplated as being variable to suit the application. The preferred range of revolution for the collars 38 is from about 0.1 to 10 revolution(s) in each direction, with 2 to 3 revolutions being especially preferred. It is also contemplated that the timing and/or amount of rotation may vary in each direction. Appropriate motor controllers (not shown) as are well known in the art are contemplated as being employable for operation of the motor 32 in this manner.

Referring again to FIG. 12, an optional feature of the apparatus 10 is the capability of varying, either constantly or intermittently, the pressure exerted by the corresponding comminution surface 114 of the ram 112 against the surface 86 of the cup 80. This pressurization has been found in some cases to reduce the formation of uncomminuted "hair balls" in the cup 80. More specifically, at least one fluid power cylinder 170, and preferably a pneumatic cylinder for each drive key 64, is provided on an upper surface 172 the drive key rack 62. A piston or control rod 174 is activated by a compressor and control valve as is known in the art (not shown) to extend a desired distance "D" and thus exert pressure against an underside of the housing lid 14. Since, during operation of the apparatus 10, the lid is secured by the latch 66, the pressure exerted by the cylinder 170 causes a downward force against the driver key 64, and ultimately, the ram 112. By controlling the pressurization of the cylinders 170, variation in the amount and timing of pressure may be exerted against the rams 112. The pressure may be intermittent, constant or not exerted at all, depending on the conditions of the particular sample.

Upon completion of the comminution process, the duration of which may vary to suit the situation, the user lifts the lid 14 and removes the sample retainer 26 as a unit or in one piece from the drive collar 38. The opening of the lid 14 disengages the ram keys 64 from the rams 112. With care being taken to avoid contamination of the comminuted sample, the technician or user removes the sample collector 72 from the nozzle 104 of the funnel 96 and processes the sample further to determine whether target substances are present as is known in the art. While it is preferred that the sample retainer 26 is disposable to avoid cross-contamination of specimens, it is also contemplated that the sample retainer may be subject to a washing and/or sterilization procedure for reuse.

While specific embodiments of the present system for comminution of multiple samples of biological specimens has been shown and described, it will be appreciated by those skilled in the art that changes and modifications may be made thereto without departing from the invention in its broader aspects and as set forth in the following claims.

What is claimed is:

1. An apparatus for comminuting biological specimens, comprising:

a receiving component provided with a drive source;

at least one sample retainer configured for accommodating at least one biological specimen and constructed and arranged for engagement in said receiving component;

said at least one sample retainer including a first component configured for receiving a specimen prior to comminution and a second component for receiving the specimen after comminution;

said first component of said at least one sample retainer being a cup with at least one first comminution surface, and said at least one sample retainer further including a ram element having at least one second comminution surface opposing said at least one first comminution surface, and said ram element being rotatably engageable with said cup so that relative rotation of said ram and said cup causes comminution of the biological specimens therebetween such that the comminuted specimens are received in said second component; and said at least one sample retainer, including said cup, said ram and said second component being insertable into and removable from said receiving component as a unit.

2. The apparatus of claim 1 wherein said drive source is configured for releasably engaging said at least one sample retainer for moving said first component relative to said ram element.

3. The apparatus of claim 2 further including at least one ram key configured for securing said ram element relative to movement of said first component, and for exerting a biasing force against said ram element for urging said ram element against said first component.

4. The apparatus of claim 1 further including a sample collector engageable upon said second component.

5. The apparatus of claim 4 further including at least one clip for securing said sample collector upon insertion into said receiving component.

6. The apparatus of claim 1 wherein said drive source is configured for moving at least two of said sample retainers simultaneously so that said ram element is rotated relative to said cup in each said retainer.

7. The apparatus of claim 6 wherein said drive source includes at least one drive collar configured for rotating a corresponding one of said cup and said second portion of each of said sample retainers and being driven by said drive source.

8. The apparatus of claim 7 wherein said drive source is a belt and pulley system.

* * * * *